United States Patent [19]

Ritter

[11] Patent Number: 5,122,519
[45] Date of Patent: Jun. 16, 1992

[54] STABLE, COSMETICALLY ACCEPTABLE TOPICAL GEL FORMULATION AND METHOD OF TREATMENT FOR ACNE

[75] Inventor: Lawrence Ritter, Suffern, N.Y.

[73] Assignee: American Cyanamid Company, Wayne, N.J.

[21] Appl. No.: 371,948

[22] Filed: Jun. 27, 1989

[51] Int. Cl.$^5$ ............................................. A61K 31/65
[52] U.S. Cl. ...................................... 514/152; 514/944
[58] Field of Search ................................ 514/152, 944

[56] References Cited

U.S. PATENT DOCUMENTS 4,058,491 11/1977 Steckler ........................ 514/944 X
4,140,656 2/1979 Mast .............................. 514/944 X
4,411,893 10/1983 Johnson et al. ................. 514/152 X

OTHER PUBLICATIONS

Chemical Abstracts, 97:3459v (1982).

Primary Examiner—Leonard Schenkman
Attorney, Agent, or Firm—Kenneth J. Dow

[57] ABSTRACT

Stable, cosmetically acceptable gel formulations of the tetracycline antibiotics for the topical treatment of acne in humans. Minocycline hydrochloride is the preferred antibiotic and the pharmaceutical vehicle is a volatile silicone solvent in combination with an emollient ester cosolvent and a polyethylene gelling agent.

22 Claims, No Drawings

STABLE, COSMETICALLY ACCEPTABLE TOPICAL GEL FORMULATION AND METHOD OF TREATMENT FOR ACNE

BACKGROUND AND PRIOR ART

This invention relates to pharmaceutical preparations and particularly to stable, cosmetically elegant topical preparations for the treatment of acne. This invention also includes a method of treatment of humans with the pharmaceutical preparations and ingredients to medicinally treat acne.

Acne is a common inflammatory disease in skin areas where sebaceous glands are largest, most numerous, and most active. In its mildest form, it is a more or less superficial disorder which is evidenced by slight, spotty skin irritations and ordinary skin hygiene is a satisfactory treatment. However, in the more inflammatory types of acne, bacterial invasion of or about the pilosebaceous follicle occurs and pustules, infected cysts, and in extreme cases canalizing inflamed and infected sacs appear. Without effective treatment, these lesions may become extensive and leave permanent, disfiguring scars.

Acne is very common in puberty. As reported by Hunnitz, S.: Clinical Pediatric Dermatology, p. 107 Philadelphia, W. B. Saunders Co., 1981, up to 85 percent of high school students have acne lesions and it is realistic to say that acne is so common 100 percent of persons between 9 and 19 have some experience with acne lesions. Usually by the early twenties the process of lesion formation slows considerably.

While acne is not a life-threatening disease, it may be cosmetically and emotionally disabling. The facial eruptions are known to cause psychic trauma. The sufferer may be constantly aware of the obvious facial blemishes. Thus, the immediate goals of treatment are to limit the physical and psychological scarring.

The etiology of lesion formation is viewed in the following way. The earliest acne lesions are comedones and are the result of the failure to normally slough the horny epidermal cells lining the follicular canal. Dilation of the orifice of a sebaceous follicle above a comedo will result in the extrusion of this mass at the surface resulting in an open comedo, a blackhead. If the pore above a comedo fails to dilate, then an impaction becomes a closed comedo or whitehead. The formation of a closed comedo can be followed by inflammatory lesions. Paules, pastules, modules and cysts may result from a process in which an impacted follicular sebaceous unit becomes the site of action of several products of Corynebacterium acnes, (P. Acnes) a normal anaerobic bacteria. Treatment of acne by a physician then becomes necessary.

Treatments that are currently used to treat acne include comedolytics, exfoliants, oral and topical bacteriostatics as well as systemic antibiotics. It is well known that the tetracycline antibiotics, and especially minocycline hydrochloride, are particularly effective in treating the condition when administered systemically. However, oral antibiotics can cause candidial vaginitis, photoreaction, onychlysis and gram-negative folliculitis, as well as headaches, dizziness and other central nervous system side effects.

Topical antibiotics offer the advantage of a decreased total absorption of the drug and an accompanying decrease in toxicity as compared with systemic antibiotics. Additionally, topical antibiotics offer the added benefit of applying the medication solely to the targeted lesions.

To reduce the severity of acne, a number of efforts have been made in the prior art to formulate topical preparations of the tetracycline antibiotics for use in acne therapy. However, these efforts have been hindered by the instability of the preparations in aqueous media. Tetracycline antibiotics are known to degrade rapidly with protic solvents to form epitetracycline, anhydrotetracycline, epianhydrotetracycline and other degradation products. These degradation products have negligible therapeutic activity. The degradation appears to start immediately upon solution and continues rapidly until an equilibrium is reached in the concentrations of tetracycline and epimer. This equilibrium point is temperature and pH dependent, with more epimer being formed at higher temperatures and lower pH. For example, at pH 4.2 and 3° C. the ratio of minocycline:epimer is about 87:13; where as at pH 2.0 and 37° C. the ratio of minocycline:epimer is 10:90. Even after this equilibrium is reached, degradation continues to take place due to oxidation and other side reactions. This leads to limited life for such tetracycline products in aqueous media.

To overcome the stability problem, the tetracycline antibiotics have been incorporated into various nonaqueous vehicles. Solutions of tetracycline antibiotics in alcohol based solvents are disclosed in U.S. Pat. Nos. 3,219,529, 3,389,174 and 4,376,118. However, the use of such alcohol based solvents have not been cosmetically acceptable due to irritation and drying of the skin. An aqueous ethanol solution of tetracycline hydrochloride in combination with an equilibrium concentration of the degradation product 4-epitetracycline hydrochloride has been commercially marketed under the trade name "Topicycline", but it is relatively unstable in its solution form due to continuous degradation. The product must be reconstituted from the powder prior to dispensing whereupon it is only stable for several months.

The tetracycline antibiotics have also been formulated in nonaqueous ointment bases, which are stable over a long period of time. While such formulations are desirable in that they are occlusive and they provide better penetration of the drug to the active site than a solution, their greasy consistency is particularly unacceptable in the treatment of acne. A formulation that is non-greasy such as a cream would be more acceptable, but most cream formulations are oil in water emulsions in which the tetracycline active ingredient is unstable.

Thus, there is a need for a topical tetracycline antibiotic preparation for the treatment of acne which is stable, provides good delivery of the drug to the skin surface, and yet is cosmetically acceptable for the purpose of acne therapy.

SUMMARY OF THE INVENTION

In accordance with the present invention, a stable gel preparation of a tetracycline antibiotic for use in the topical treatment of acne in humans is provided Which is easy to apply, non-greasy, soft, non-irritating to the site of administration and cosmetically appealing to the user. A typical composition of the present invention comprises a mixture of a tetracycline antibiotic, a nonvolatile silicone solvent, and an emollient cosolvent in combination with a pharmaceutically acceptable gelling agent such as polyethylene. Preferably, the tetracycline antibiotic is 7-dimethylamino-6-deoxy-6-demethyltetracycline hydrochloride also known as minocycline hydrochloride.

DESCRIPTION OF THE INVENTION

The antibiotics used in the present invention are the tetracycline compounds in general, and special mention is made of the use of members of the tetracycline family comprising substituted 4-, 7-, and 9-aminotetracyclines which may be represented by the following general formula:

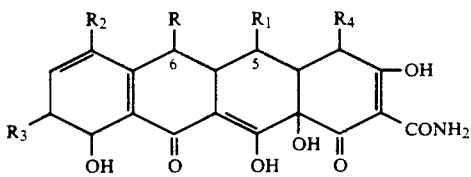

where R is hydrogen or methyl, $R_1$ is hydrogen or hydroxyl, and $R_2$, $R_3$ and $R_4$ are hydrogen, mono(lower alkyl)amino or di(lower alkyl)amino with the proviso that $R_2$, $R_3$ and $R_4$ cannot all be hydrogen. Typical compounds represented by the above general formula are, for example,
7-methylamino-6-deoxy-6-demethyltetracycline,
7-ethylamino-6-deoxy-6-demethyltetracycline,
7-isopropylamino-6-deoxy-6-demethyltetracycline,
9-methylamino-6-deoxy-6-demethyltetracycline,
9-ethylamino-6-deoxy-6-demethyltetracycline,
9-isopropylamino-6-deoxy-6-demethyltetracycline,
7,9-di(ethylamino)-6-deoxy-6-demethyltetracycline,
7-dimethylamino-6-deoxy-6-demethyltetracycline,
9-dimethylamino-6-deoxy-6-demethyltetracycline,
7-methylamino-6-deoxytetracycline,
9-ethylamino-6-deoxytetracycline,
7,9-di(mothylamino)-6-deoxytetracycline,
7-diethylamino-6-deoxytetracycline,
9-diethylamino-6-deoxytetracycline,
7,9-di(methylethylamino)-6-deoxytetracycline,
7-methylamino-9-ethylamino-6-deoxytetracycline, and
9-methylamino-5-hydroxy-6-deoxytetracycline.

Preferred members of this family comprise tetracycline compounds selected from:
(a) 7-dimethylamino-6-deoxy-6-demethyltetracycline;
(b) 7-methylamino-6-deoxy-6-dimethyl-tetracycline;
(c) 9-methylamino-6-deoxy-6-demethyltetracycline;
(d) 7-ethylamino-6-deoxy-6-demethyltetracycline;
(e) 7-isoproplamino-6-deoxy-6-demethyltetracycline;
(f) 6-deoxy-5-oxytetracycline
(g) a non-toxic acid addition salt or hydrate of (a)-(f), inclusive or
(h) a mixture of any of the foregoing.

Specific examples of the preferred antibiotic agents include: tetracyclines (tetracycline, minocycline, doxycycline, oxytetracycline, chlortetracycline, demeclocycline, methacycline), and the pharmaceutically acceptable salts or hydrates of the foregoing.

Special mention is made of the tetracycline compounds, 7-dimethylamino-6-deoxy-6-demethyltetracycline, 6-deoxy-5-oxytetracycline and their non-toxic acid addition salts or hydrates, e.g., hydrochloric, sulfonic, trichloroacetic acid salts, and the like, especially the hydrochloric acid addition salts. The first named compound in the form of its monohydrochloride is also known as minocycline and the second named compound is also known in the form of its monohydrate as doxycycline hyclate. These compounds and methods for their preparation are disclosed in U.S. Pat. Nos. 3,148,212, 3,200,149 and 3,226,436.

Minocycline is a potent semisynthetic tetracycline analog with activity against a wide range of gram-positive and gram-negative organisms. It has been shown to be particularly effective as adjunctive therapy in the treatment of severe acne possibly because of its lipid solubility which provides better penetration of the drug to the active site.

Accordingly, by using the composition of the present invention for treating acne, side effects due to oral administration of a tetracycline, minocycline, doxycycline, and the like, such as those of the digestive system, for example, anorexia, nausea and diarrhea, glossitis, enterocolitis and monilial overgrowth as well as potentially serious biochemical abnormalities such as thrombocytopenia and eosinophilia can be reduced. As a result, the topical composition of the present invention is very useful from the clinical point of view.

The fundament of the instant invention resides in the discovery that minocycline can be formulated in a remarkably unexpected stable gel for topical application to a human with acne lesions. The formulation has advantages over typical petroleum grease base ointments in that it is non-greasy, efficacious, non-irritating, easily rubbed in by local administration leaving no visible residue and has the cosmetic elegance of a cream. Additionally, non- staining of the skin or clothing promotes patient acceptance. The exceptional stability of the minocycline hydrochloride gel formulation eliminates the need for any reconstitution from the powder prior to dispensing and saves the patient expense because there is no need for special storage or frequent replacement.

In the present preparation we prefer to use a solvent selected from, but not limited to, the following group of volatile silicones:
cyclomethicone(octamethylcyclotetrasiloxane),
cyclomethicone(decamethylcyclopentasiloxane),
hexamethyldisiloxane or mixtures thereof.

In addition, as cosolvent in the preparation we prefer to use an emollient selected from, but not limited to, the following group: isopropyl palmitate, isopropyl myristate, isopropyl stearate, diisopropyl adipate, C12-15 alcohols benzoate, tridecyl neopentanoate, tridecyl octanoate, propylene glycol dipelargonate, octyl octanoate, octyl stearate, polypropylene glycol-2 myristyl ether propionate, octyl salicylate, octyl methoxycinnanate, isodecyl neopentanoate or mixtures thereof.

In accordance with the present invention we prefer to use in combination with the solvent and cosolvent mixture, a gelling agent selected from the group of polyethylene homopolymers and copolymers, including but not limited to the following: homopolymers oxidized homopolymers, copolymers/acrylic acid copolymers/vinyl acetate, and mixtures thereof.

A stable composition of the present invention generally comprises the following tetracycline antibiotic gel:
Tetracycline antibiotic . . . 0.1–10.0% w/w
Gelling agent . . . 1.0–40.0% w/w
Cosolvent . . . 5.0–75.0% w/w
Solvent qs . . . 20.0–70.0% w/w A specific formulation is as follows:
Minocycline hydrochloride . . . 0.1–5.0% w/w
Gelling agent . . . 1.0–40.0% w/w
Cosolvent . . . 5.0–75.% w/w
Solvent qs . . . 20.0–70.0% w/w A preferred stable composition of this invention comprises a gel of the following composition:
Tetracycline antibiotic ... 1.0% w/w
Gelling agent ... 17.0% w/w
Cosolvent ... 41.0% w/w
Solvent qs ad ... 100.0% w/w A more preferred composition of this invention comprises a gel of the following composition:
Minocycline ... 1.0% w/w
Gelling agent ... 17.0% w/w
Cosolvent ... 41.0% w/w
Solvent qs ad ... 100.0% w/w A most preferred composition of this invention comprises a gel of the following composition:
Minocycline hydrochloride ... 1.0% w/w
Polyethylene ... 17.0% w/w
Isopropyl palmitate ... 41.0% w/w
Cyclomethicone qs ad ... 100.0% w/w The composition is conveniently prepared in the following manner. The cosolvent and a portion of the solvent are mixed in a steam jacketed kettle. The gelling agent is added in the form of dry granules and dissolved at an elevated temperature with gentle agitation. When a clear solution is obtained the balance of the solvent is slowly added with continued agitation. Cold water is then circulated through the jacket to initiate gelation while agitation is continued. The tetracycline antibiotic is dispersed in a portion of the solvent-cosolvent mixture using an agitator, then is passed as required through a rotor-stator type colloid mill when the temperature of the main batch mixture is sufficiently cooled the tetracycline antibiotic dispersion is added and agitation is continued until dispersion is complete. The mixture is adjusted to the final desired potency by adding solvent. Cold water circulation is continued until there is sufficient gelation. Agitation is then suspended and the batch is filled into suitable final containers.

More specifically, to prepare this composition of matter the isopropyl palmitate and a portion of the cyclomethicone are mixed in a steam jacketed kettle. The polyethylene (Allied Corp., Morristown, N.J. No. AC617A) is added in the form of dry granules and dissolved at 90°-95° C. with gentle agitation. When a clear solution is obtained the balance of the cyclomethicone is slowly added with continued agitation. Cold (20°-25° C.) water is then circulated through the jacket to initiate gelation while agitation is continued. The minocycline hydrochloride is dispersed in a portion of the solvent-cosolvent mixture using an agitator, then is passed as required through a rotor-stator type colloid mill. When the temperature of the main batch mixture reaches approximately 55° C., the minocycline hydrochloride dispersion is added and agitation is continued until dispersion is complete.

The mixture is adjusted to the final desired potency by adding cyclomethicone and cold water while circulation is continued until the batch temperature reaches 35°-40° C. Agitation is then suspended and the batch is filled into suitable final containers.

The invention has a stability which should allow a 3+ year shelf life at controlled room temperature. The compositions of the present invention have been stored for extended periods of time at 23° C., 37° C. and 42° C. without significant degradation. No special storage conditions are required (such as storage as a dry powder and reconstitution just before use as the product "Topicycline" employs).

The following example displays a comparison of this invention to aqueous systems. Any formulations which utilizes a protic solvent will experience the rapid drug potency loss demonstrated for aqueous systems.

EXAMPLE 1

A control composition (Sample A) consisting of an aqueous solution of minocycline hydrochloride, with sufficient buffer to maintain a pH of 4.2 was prepared having the following composition:

| SAMPLE A | |
|---|---|
| | Percent (Weight/Volume Basis) |
| Minocycline Hydrochloride | 0.01* |
| Sodium Phosphate Monobasic, Monohydrate | 0.0138 |
| Phosphoric Acid | q.s. pH 4.2 |
| Purified Water | q.s. 100.00 |

*as Minocycline neutral

A test mixture (Sample B) was prepared having the following composition:

| SAMPLE B | |
|---|---|
| | Percent (Weight/Weight Basis) |
| Minocycline Hydrochloride | 3.0* |
| Isopropyl Palmitate | 41.4 |
| Polyethylene homopolymer A-C 617A (A-C ® Polyethylenes, Allied Signal Corp., Morristown, New Jersey) | 17.2 |
| Silicone 244 Fluid (cyclomethicone - Dow Corning, Midland, Michigan). | q.s. |
| | 100.0 |

*as Minocycline neutral

Appropriate samples of the above two compositions were stored at varying temperatures for extended periods. The samples were periodically assayed, using the procedures outlined below, for minocycline and the degradation product epi-minocycline. The results are shown in the following Tables I and II.

TABLE I

Percentage of Initial Potency Remaining After Storage Minocycline HCL in Aqueous Phosphate Buffer (Sample A)

| Time (Days) | % of Initial Assay | | |
|---|---|---|---|
| | 3° C. | 23° C. | 37° C. |
| 0 | 100 | 100 | 100.0 |
| 0.208 | 103 | 100.5 | 87.5 |
| 1 | 99.7 | 88.2 | 69.6 |
| 3 | 94.3 | 76.8 | 60.5 |
| 6 | 87.4 | 68.6 | 54.5 |
| 7 | 93.2 | 68.9 | 54.3 |
| 10 | 88.2 | 67.5 | 43.1 |
| 14 | 87.3 | 67.7 | 43.2 |
| 17 | 77.9 | 60.8 | 32.8 |
| 21 | 79.6 | 60.7 | 32.2 |
| 24 | 79.9 | 61.7 | — |
| 29 | 80.2 | 62.0 | 27.0 |

TABLE II

Percentage of Initial Potency Remaining After Storage Minocycline HCL Topical Gel 3% (Sample B)

| Time (Months) | % of Initial Assay | | |
|---|---|---|---|
| | 23° C. | 37° C. | 42° C. |
| 0 | 100.0 | — | — |
| 1 | 100.4 | 100.1 | 99.1 |

TABLE II-continued

Percentage of Initial Potency Remaining After Storage Minocycline HCL Topical Gel 3% (Sample B)

| Time (Months) | % of Initial Assay | | |
|---|---|---|---|
| | 23° C. | 37° C. | 42° C. |
| 2 | 99.8 | 97.8 | 101.3 |
| 3 | 98.3 | 99.8 | 97.9 |
| 6 | 100.6 | — | — |

A comparison of the data outlined in Tables I and II shows that the composition of the present invention is stable over an extended period of time and is considerably more stable than a formulation using an aqueous vehicle. Under acidic conditions (pH 4.2) at room temperature and below, the major reaction pathway for the degradation of the aqueous solution was epimerization and subsequent equilibration of minocycline and its C-4 epimer. At higher temperatures and longer periods of time, additional products were formed.

The above data on the minocycline and epi-minocycline degradation products of the various compositions were obtained using a high performance liquid chromatographic-spectrophotometric method. The assay conditions for the minocycline gel formulation were as follows:

Column: Supelcosil LC-8, 5 micron packing, 150×4.6 mm, available from Supelco Inc. or equivalent.

Solvent System: 50% Dimethylformamide 50% Methanol

Mobile Phase: Dimethylformamide/EDTA/ammonium oxalate at 2.0 ml/min

Detector: Ultraviolet at 280 nm and 0.05 AUFS

What is claimed is:

1. A stable, cosmetically elegant gel formulation for the topical treatment of acne in humans comprising an effective amount of a compound selected from the group consisting of those of the formulae:

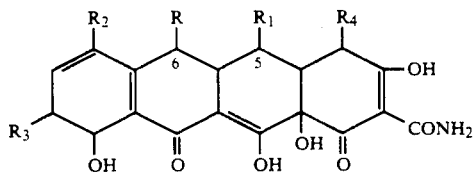

where R is hydrogen or methyl, $R_1$ is hydrogen or hydroxyl, and $R_2$, $R_3$ and $R_4$ are hydrogen, mono(lower alkyl)amino or di(lower alkyl)amino with the proviso that $R_2$, $R_3$ and $R_4$ cannot all be hydrogen or the non-toxic addition salts or hydrates thereof at a concentration of 0.10% to 10.0% w/w in a pharmaceutical vehicle comprising:
(a) about 1.0% to 40.0% w/w of a gelling agent comprised of:
  (i) a polyethylene homopolymer; or
  (ii) a polyethylene/vinyl acetate copolymer; or
  (iii) a polyethylene/acrylic acid copolymer; or
  (iv) any combination thereof;
(b) about 5.0% to 75% w/w of an emollient ester cosolvent; and
(c) about 20.0% to 70% w/w of a volatile silicone solvent.

2. A composition according to claim 1 in which the tetracycline antibiotic is 7-dimethylamino-6-deoxy-6-demethyltetracycline and its non-toxic acid addition salts or hydrates such as hydrochloric, sulfonic, trichloroacetic acid salts.

3. A composition according to claim in which the tetracycline antibiotic is 7-dimethylamino-6-deoxy-6-demethyltetracycline as its hydrochloride salt which is known as minocycline hydrochloride.

4. A composition according to claim 1, in which the tetracycline antibiotic concentration is about 1.0% w/w.

5. A composition according to claim 1 in which the tetracycline antibiotic is 6-deoxy-5-oxytetracycline and its non-toxic acid addition salts or hydrates such as hydrochloric, sulfonic, trichloroacetic acid salts.

6. A composition according to claim 1 in which the tetracycline antibiotic is 6-deoxy-5-oxytetracycline as its monohydrate known as doxycycline hyclate.

7. A composition according to claim 1 in which the solvent is selected from the group of silicones comprising cyclomethicone (octamethylcyclotetrasiloxane), cyclomethicone (decamethylcyclopentasiloxane), hexamethyldisiloxane and mixtures thereof.

8. A composition according to claim 7 in which the solvent is cyclomethicone in a concentration of about 20.0–70.0% w/w.

9. A composition according to claim 8 in which the solvent cyclomethicone is in a concentration of about 41.0%.

10. A composition according to claim 1 in which the cosolvent is selected from a group of emollients comprising: isopropyl palmitate, isopropyl myristate, isopropyl stearate, diisopropyl adipate, $C_{12-15}$ alcohols benzoate, tridecyl neopentanoate, tridecyl octanoate, propylene glycoldipelargonate, octyl octanoate, octyl stearate, polypropylene glycol-2 myristyl ether propionate, octyl salicylate, octyl methoxycinnanate, isodecyl neopentanoate and mixtures thereof.

11. A composition according to claim 10 in which the cosolvent is isopropyl palmitate in a concentration of about 5.0–75.0% w/w.

12. A composition according to claim 11 in which the cosolvent isopropyl palmitate is in a concentration of 41.0%.

13. A composition according to claim 1 in which the gelling agent is in a concentration of 17.0% w/w.

14. A composition of matter according to claim 1 in which the ingredients are:
Minocycline hydrochloride . . . 0.10–5.0% w/w
gelling agent . . . 1.0–40.0% w/w
Isopropyl palmitate . . . 5.0–75.0% w/w
Cyclomethicone . . . 20.0–70.0% w/w 15. A composition of matter according to claim 1 in which the ingredients are:
Minocycline hydrochloride . . . 1.0% w/w
gelling agent . . . 17.0% w/w
Isopropyl palmitate . . . 41.0% w/w
Cyclomethicone qs ad . . . 100.0% w/w 16. A method of treating acne in a human comprising the topical application of an effective amount of the anti-acne composition of claim 1 to said patient.

17. A method of treating acne in a human comprising the topical application of an effective amount of the anti-acne composition of claim 14 to said patient.

18. A method of treating acne in a human comprising the topical application of an effective amount of the anti-acne composition of claim 17 to said patient.

19. A method of treating acne in humans comprising topically applying to said human an effective amount of the composition according to claim 1, in which the compound is 7-dimethylamino-6-deoxy-6-demethyltetracycline and its non-toxic acid addition salts or hydrates such as hydrochloric, sulfonic, trichloro-acetic acids salts.

20. A method according to claim 19 in which the compound is 7-dimethylamino-6-deoxy-6-demethyltetracycline as its hydrochloride salt also known as minocycline hydrochloride.

21. A method of treating acne in humans comprising topically applying to said human an effective amount of a composition according to claim 1 in which the compound is 6-deoxy-5-oxytetracycline and its non-toxic acid addition salts or hydrates such as hydrochloric, sulfonic, trichloroacetic acid salts.

22. A method according to claim 21 in which the compound 6-deoxy-5-oxytetracycline in its monohydrate also known as doxycycline hyclate.

* * * * *